(12) United States Patent
Chiang

(10) Patent No.: US 6,875,188 B2
(45) Date of Patent: Apr. 5, 2005

(54) SUPPORT BANDAGE FOR A JOINT BETWEEN BONES

(76) Inventor: Pang-Ching Chiang, 6F, No. 293, Sec. 4, Chung-Hsiao E. Rd., Taipei (TW)

( * ) Notice: Subject to any disclaimer, the term of this patent is extended or adjusted under 35 U.S.C. 154(b) by 0 days.

(21) Appl. No.: 10/653,197

(22) Filed: Sep. 3, 2003

(65) Prior Publication Data

US 2005/0049536 A1 Mar. 3, 2005

(51) Int. Cl.[7] ................................................. A61F 5/00
(52) U.S. Cl. .............................. 602/7; 602/26; 602/63; 602/901; 128/882
(58) Field of Search ........................... 602/7, 19, 20, 602/21, 23, 24, 25, 26, 62, 63, 75, 76, 77, 901; 128/878, 882, 870, 856; 2/16, 22

(56) References Cited

U.S. PATENT DOCUMENTS

| | | | | |
|---|---|---|---|---|
| 4,492,227 A | * | 1/1985 | Senn et al. ................... | 602/63 |
| 5,411,037 A | * | 5/1995 | Hess et al. .................. | 128/882 |
| 5,656,023 A | * | 8/1997 | Caprio et al. ................. | 602/63 |
| 5,865,776 A | * | 2/1999 | Springs ........................ | 602/26 |
| 5,865,777 A | * | 2/1999 | Detty ........................... | 602/26 |
| 6,063,048 A | * | 5/2000 | Bodenschatz et al. ........ | 602/62 |
| 6,117,097 A | * | 9/2000 | Ruiz ............................ | 602/26 |
| 6,156,001 A | * | 12/2000 | Frangi et al. ................. | 602/75 |
| 6,592,539 B1 | * | 7/2003 | Einarsson et al. ............ | 602/62 |

* cited by examiner

*Primary Examiner*—Fadi H. Dahbour
(74) *Attorney, Agent, or Firm*—Rabin & Berdo, P.C.

(57) ABSTRACT

A support bandage for a joint between bones includes a small fraction having two opposite first longitudinal sides sewn with two opposite second longitudinal sides of a large fraction. The small fraction is incurved towards the large fraction, and has two arcuate seams on the small fraction. The segment between the two arcuate seams is more incurved than two end segments outside the arcuate seams, and the two arcuate seams are away from a wearer's joint. Whereby, the support bandage can be tightly abut a knee or an elbow yet have few wrinkles and will not uncomfortably press the wearer.

2 Claims, 6 Drawing Sheets

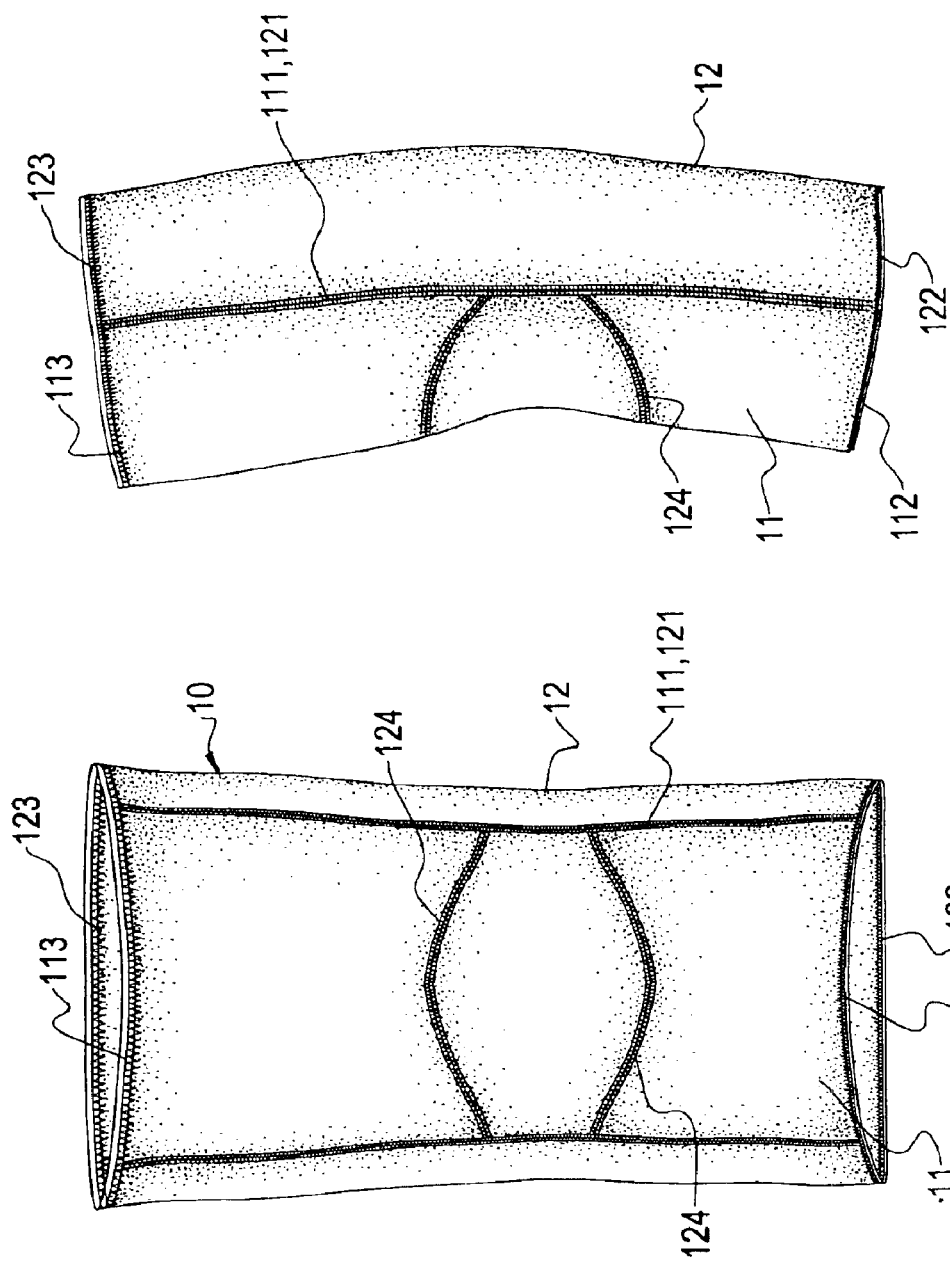

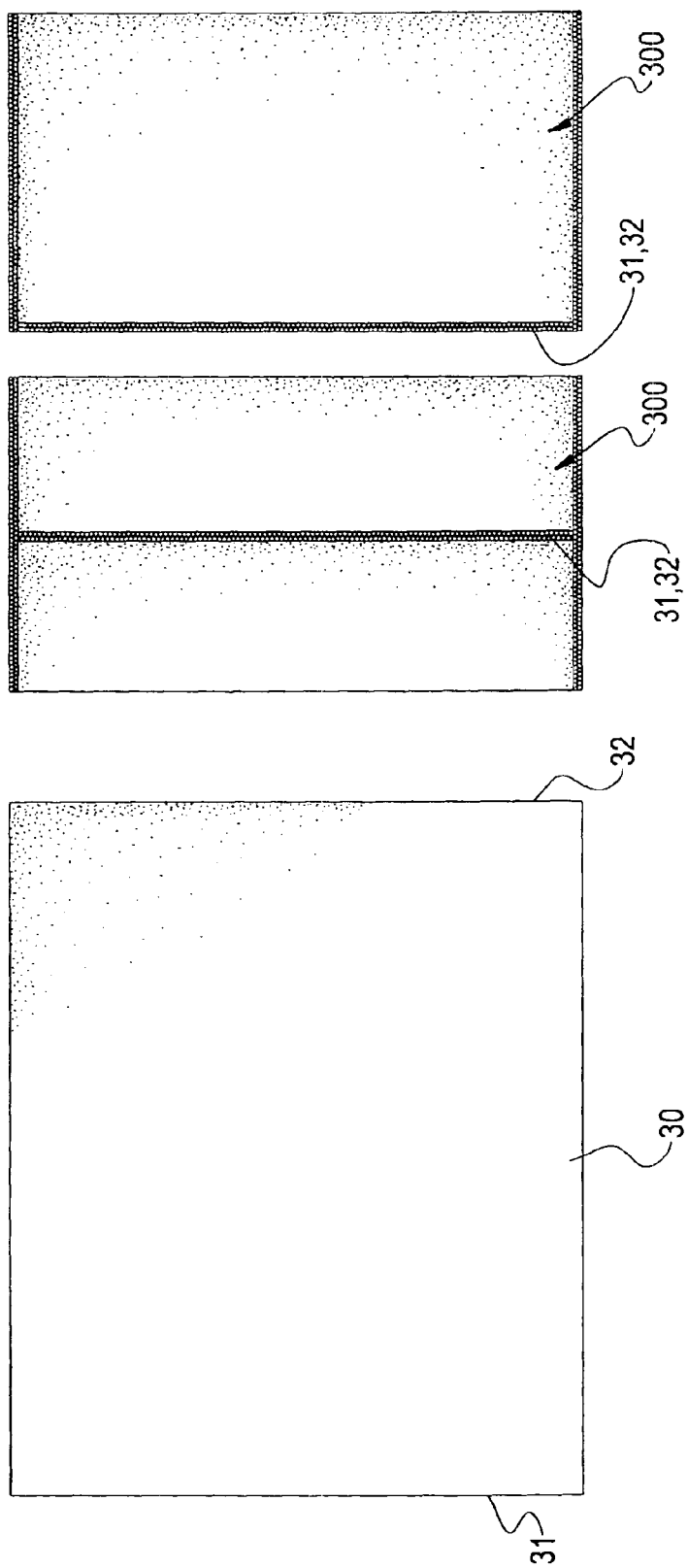

US 6,875,188 B2

SUPPORT BANDAGE FOR A JOINT BETWEEN BONES

BACKGROUND OF THE INVENTION

1. Field of the Invention

The present invention relates a support bandage to protect a wearer's joint such as knee or elbow.

2. Description of Related Art

In sports, players often wear elastic bandage to protect their joints such as knees and elbows. With reference to FIG. 4, a first conventional support bandage for a joint between bones is formed by a rectangular cloth (30) with two opposite longitudinal sides (31, 32). The longitudinal sides (31, 32) are sewn up to form a tubular support bandage (300) (as shown in FIGS. 5a and b). With reference to FIG. 6, when a joint with the support bandage (300) is bent, there are a lot of wrinkles formed at the interior side of the support bandage, and the wearer will feel discomfort.

With reference to FIGS. 7 and 8, another improved support bandage for a joint between bones (400) is formed with a rectangular cloth (40) with two triangular notches (43) defined at two opposite longitudinal sides (41, 42). The triangular notches (43) are sewn up before the longitudinal sides (41, 42) are sewn up. Thus, the support bandage (400) is incurved at the longitudinal sides (41, 42) sewn together. Compared with the first conventional support bandage (300), the incurved portions of the support bandage (400) can match the contour of the joint. However, the notches (43) are defined in the middle of the cloth (40), and the seams of the notches (43) will press the joint to make the wearer uncomfortable. Furthermore, the curve of the support bandage (400) caused by the sewn notches (43) is not smooth, and there are still some wrinkles formed at the interior side which can cause physical irritation to the wearer.

Therefore, the invention provides a support bandage to mitigate and/or obviate the aforementioned problems.

SUMMARY OF THE INVENTION

The main objective of the invention is to provide a support bandage for a joint between bones which has a smooth curve and few wrinkles whereby the wearer's joint is supported in a comfortable manner.

Other objectives, advantages and novel features of the invention will become more apparent from the following detailed description when taken in conjunction with the accompanying drawings.

BRIEF DESCRIPTION OF THE DRAWINGS

FIGS. 3A and 3B are front and side views of the support bandage in FIG. 2;

FIG. 4 is a schematic view of a spread cloth to form a first conventional support bandage;

FIGS. 5A and 5B are front and side views of the first conventional support bandage;

DETAILED DESCRIPTION OF THE PREFERRED EMBODIMENT

Figure 1:
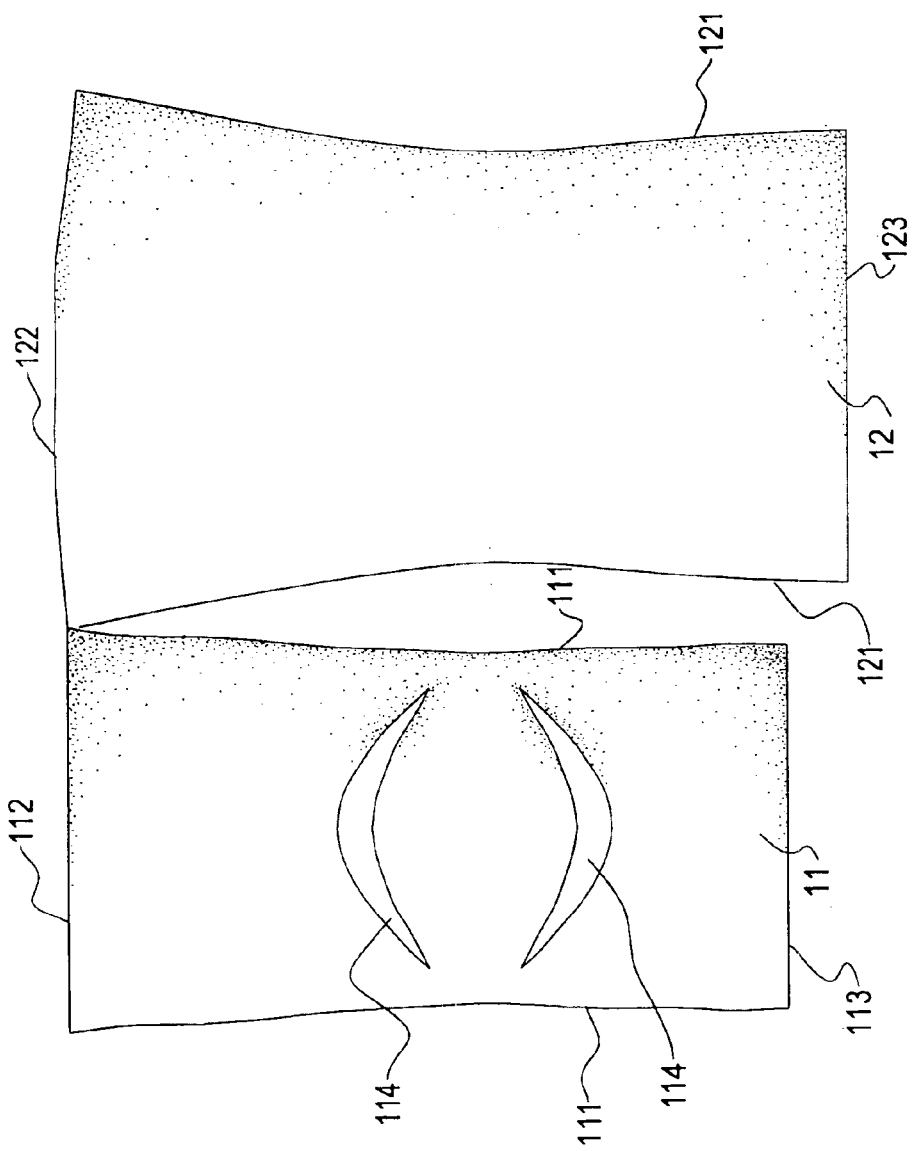
FIG. 1 is a schematic view of a spread cloth to form a support bandage for a joint between bones in accordance with the invention in the spread status.

With reference to FIG. 1, an elastic cloth to form a support bandage for a joint between bones (10) in accordance with the invention is cut into a small fraction (11) and a large fraction (12) partially connected together.

The small fraction (11) has two opposite first longitudinal sides (111), a first top side (112) and a first bottom side (113); and the large fraction (12) has two opposite second longitudinal sides (121), a second top side (122) and a second bottom side (123). The two fractions (11, 12) are connected at two top corners thereof, and the first longitudinal sides (111) are shorter than the second longitudinal sides (121).

The second longitudinal sides (121) are incurved, and the second top side (122) is slightly longer than the second bottom side (123). The first longitudinal sides (111) are also incurved. Two crescent openings (114) are defined through the small fraction (11), wherein the upper opening (114) is curved upwards and the lower opening (114) is curved downwards, and each opening (114) has a middle portion (not numbered) wider than two end portions (not numbered).

Figure 2:
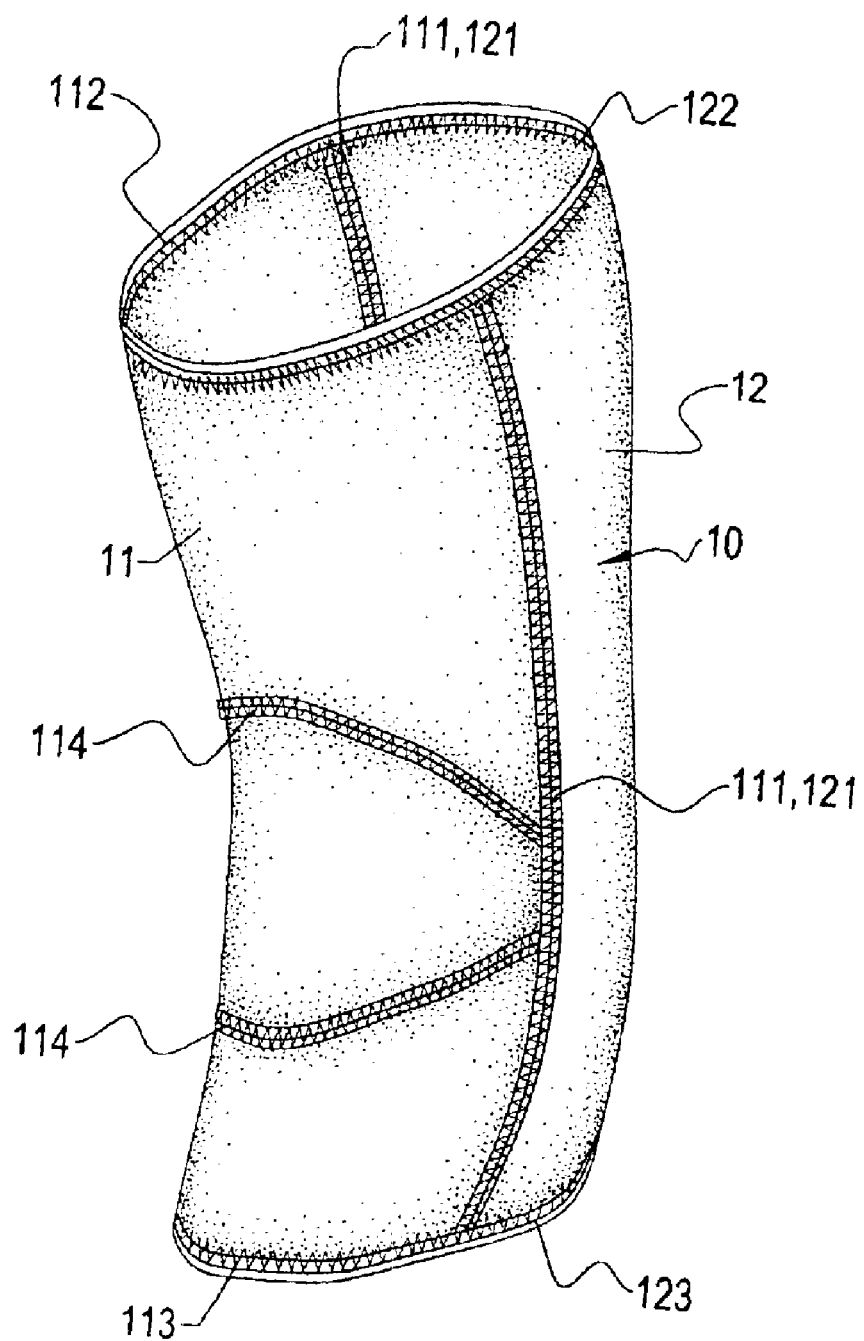
FIG. 2 is a perspective view of the support bandage in accordance with the invention.
Figure 6:
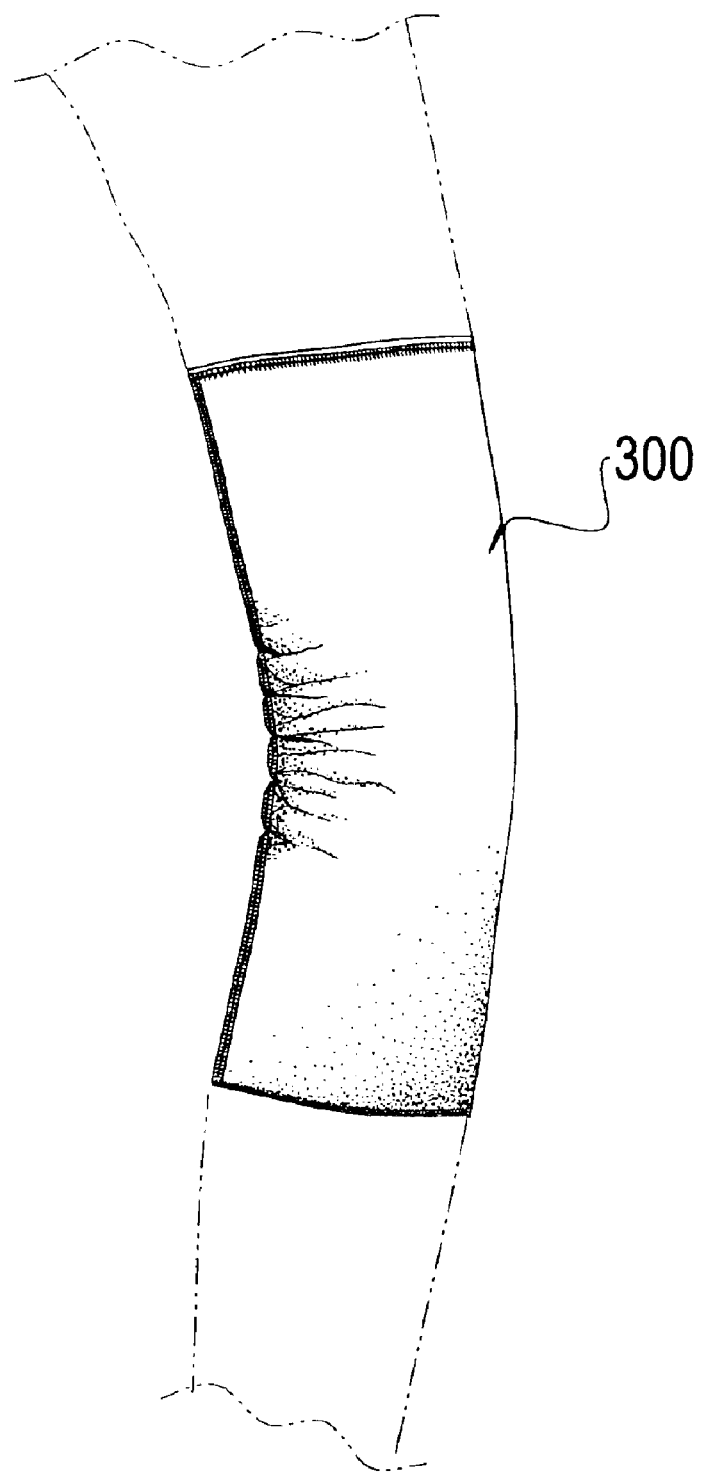
FIG. 6 is a schematic view of the first conventional support bandage.
Figures 7A, 7B, 8:
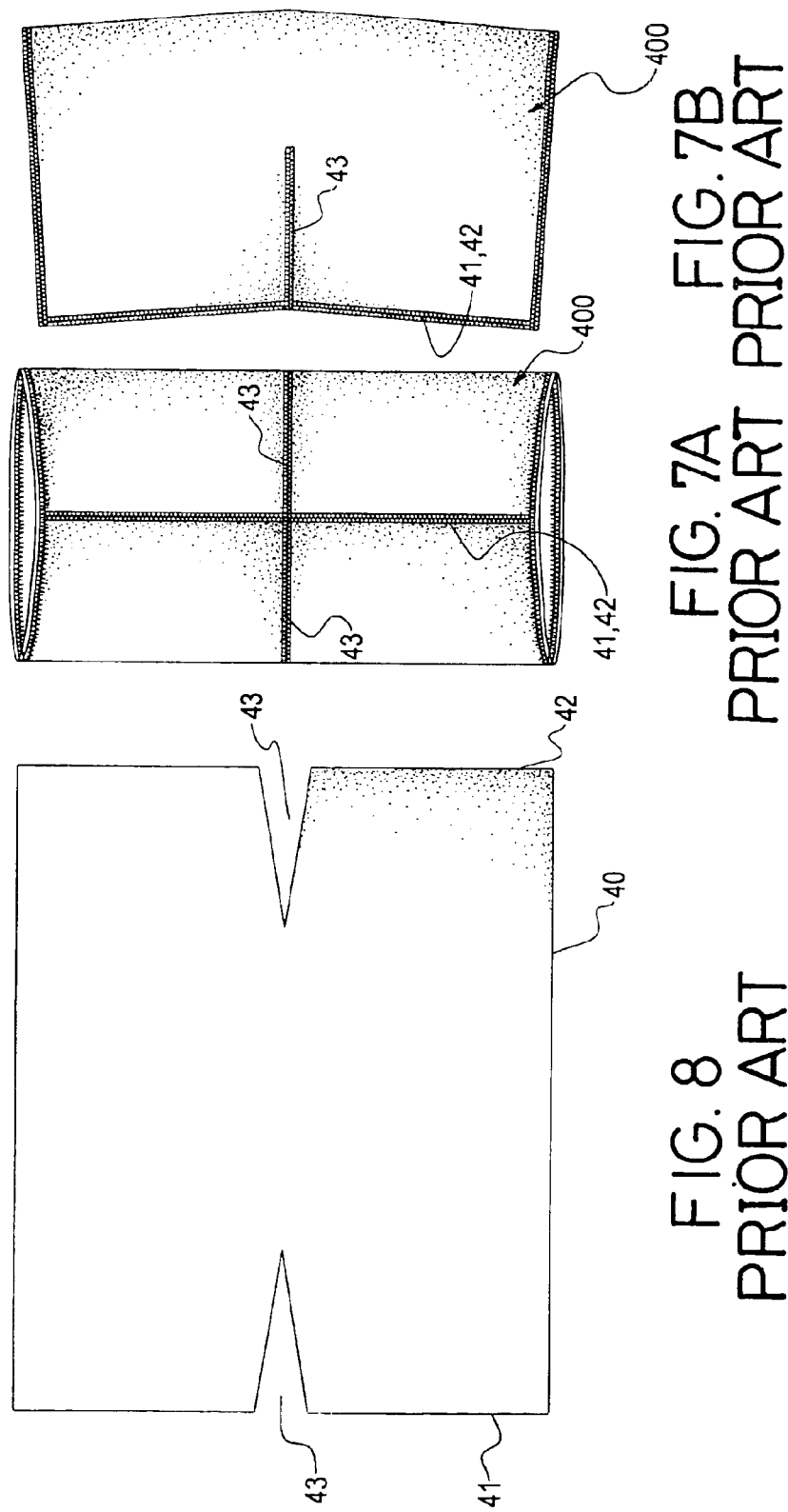
FIGS. 7A and 7B are front and side views of a second conventional support bandage.
FIG. 8 is a schematic view of a spread cloth to form the second conventional support bandage.

In sewing, the interior sides (not numbered) of the two crescent openings (114) are sewn up to close the crescent openings (114), and the first longitudinal sides (111) are respectively sewn with the second longitudinal sides (121) to form the tubular sleeve (10) as shown in FIG. 2.

With reference to FIG. 3, because the small fraction (11) is shorter than the large fraction (12), the small fraction (11) has a shortest length at the central line between the two first longitudinal sides (111), and the large fraction (12) has a longest length at the central line between the two second longitudinal sides (121), so the small fraction (11) is incurved towards the large fraction (12). Because the crescent openings (114) have the middle portions wider than the end portions, the segment between the two openings (114) is more incurved than the two end segments outside the openings (114). Therefore, when the support bandage (10) is worn on a knee or an elbow, the incurved portions of the small fraction (11) can tightly abut the joint with few wrinkles, and the seams of the openings (114) are away from the joint and will not press the wearer.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A support bandage for a joint between bones, comprising:

a small fraction having two opposite first longitudinal sides; and a large fraction having two opposite second longitudinal sides, the first longitudinal sides being respectively sewn to the second longitudinal sides, wherein the small fraction is incurved towards the large fraction, and has two arcuate seams, with a segment between the two arcuate seams being more incurved than two end segments outside the arcuate seams, the two arcuate seams being locatable at an inside of a wearer's joint;

wherein before being sewn up, the small fraction has a first top side and a first bottom side between the first longitudinal sides, and a crescent upper opening and a crescent lower opening, the upper opening being curved upwards and the lower opening being curved downwards, each opening having a middle portion that is wider than two end portions, the first longitudinal sides being incurved; and wherein the large fraction has a second top side and a second bottom side between the second longitudinal sides, the second longitudinal sides being incurved.

2. The support bandage for a joint between bones as claimed in claim 1, wherein the small fraction and the large fraction are connected at an upper corner.

* * * * *